US00PP14642P29

(12) United States Plant Patent
Smith et al.

(10) Patent No.: US PP14,642 P2
(45) Date of Patent: Mar. 30, 2004

(54) ARGYRANTHEMUM PLANT NAMED 'VANILLA'

(50) Latin Name: *Argyranthemum frutescens*
Varietal Denomination: Vanilla

(75) Inventors: Tom Smith, Carleton, MI (US); Michael R. Heulitt, Carleton, MI (US); Sandra Metzger, LaSalle, MI (US); Debbie Avery, Newport, MI (US)

(73) Assignee: Four Star Greenhouse, Carlton, MI (US)

( * ) Notice: Subject to any disclaimer, the term of this patent is extended or adjusted under 35 U.S.C. 154(b) by 0 days.

(21) Appl. No.: 10/452,072

(22) Filed: Jun. 2, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A new and distinct cultivar of Argyranthemum plant named 'Vanilla', characterized by its compact, mounded, upright and outwardly spreading plant habit; freely branching habit, short internodes; dense and bushy plants; freely and continuous flowering habit with numerous inflorescences per plant held above the foliage; large single daisy inflorescence form with yellow-colored ray florets that become mostly white with development; bright yellow-colored disc florets; and good garden performance.

1 Drawing Sheet

Botanical classification/cultivar denomination: *Argyranthemum frutescens* cultivar Vanilla.

BACKGROUND OF THE INVENTION

The present invention relates to a new and distinct cultivar of Argyranthemum plant, botanically known as *Argyranthemum frutescens* and hereinafter referred to by the cultivar name 'Vanilla'.

The new Argyranthemum is a naturally-occurring whole plant mutation of the *Argyranthemum frutescens* cultivar Butterfly, not patented. The new Argyranthemum was discovered and selected by the Inventors as a single plant within a population of plants of the cultivar Butterfly in a controlled environment in Carlton, Mich. in September, 2001. The new Argyranthemum was selected on the basis of its ray floret coloration.

Asexual reproduction of the new Argyranthemum by terminal cuttings taken in a controlled environment in Carlton, Mich. since September, 2001, has shown that the unique features of this new Argyranthemum are stable and reproduced true to type in successive generations.

SUMMARY OF THE INVENTION

The new Argyranthemum has not been observed under all possible environmental conditions. The phenotype may vary somewhat with variations in environment such as temperature and light intensity without, however, any variance in genotype.

The following characteristics have been repeatedly observed and are determined to be basic characteristics of 'Vanilla' and distinguish the new Argyranthemum as a new and distinct cultivar:

1. Compact, mounded, upright and outwardly spreading plant habit.
2. Freely branching habit, short internodes; dense and bushy plants.

3. Freely and continuous flowering habit with numerous inflorescences per plant held above the foliage.
4. Large single daisy inflorescence form with yellow-colored ray florets that become mostly white with development.
5. Bright yellow-colored disc florets.
6. Good garden performance.

Plants of the new Argyranthemum are most similar to plants of the parent, the cultivar Butterfly. However, plants of the new Argyranthemum differ from plants of the cultivar Butterfly in the following characteristics:

1. Plants of the new Argyranthemum have slightly smaller leaves and inflorescences than inflorescences of plants of the cultivar Butterfly.
2. Plants of the new Argyranthemum are more freely flowering than plants of the cultivar Butterfly.
3. Inflorescences of plants of the new Argyranthemum have a faint pleasant fragrance whereas inflorescences of plants of the cultivar Butterfly are not fragrant.
4. Fully expanded ray florets of the new Argyranthemum are mostly white in color whereas fully expanded ray florets of plants of the cultivar Butterfly are yellow in color.
5. Plants of the new Argyranthemum have shorter involucral bracts than plants of the cultivar Butterfly.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Argyranthemum.

The photograph at the top of the sheet comprises a side perspective view of a typical flowering plant of 'Vanilla' grown in a container.

The photograph at the bottom of the sheet comprises a close-up view of typical developing inflorescences and flowering stems of 'Vanilla'.

DETAILED BOTANICAL DESCRIPTION

The aforementioned photographs, following observations and averaged measurements describe plants grown in Carlton, Mich., in an outdoor nursery with day temperatures ranging from 23 to 29° C., night temperatures ranging from 12 to 17° C. and light levels about 8,000 to 10,000 foot-candles. Plants were grown for about 15 weeks in 22-cm containers. Color references are made to The Royal Horticultural Society Colour Chart, 1995 Edition, except where general terms of ordinary dictionary significance are used.

Botanical classification: *Argyranthemum frutescens* cultivar Vanilla.

Parentage: Naturally-occurring whole plant mutation of *Argyranthemum frutescens*, not patented.

Propagation:

*Type.*—Terminal vegetative cuttings.

*Time to initiate roots.*—About 7 to 10 days at 19° C.

*Time to produce a rooted cutting.*—About 28 to 32 days at 19° C.

*Root description.*—Fibrous; moderately thick to thick; white, close to 155D, in color.

*Rooting habit.*—Freely branching; dense.

Plant description:

*General appearance.*—Inverted triangle; compact, mounded, upright and outwardly spreading plant form with short internodes, dense foliage and numerous inflorescences held above the foliage on long peduncles. Vigorous growth habit.

*Plant height.*—About 30 to 40 cm.

*Plant width, per plant.*—About 60 to 70 cm.

*Lateral branch description.*—Quantity per plant: Freely branching; about 12 to 15 primary lateral branches; each with about 7 to 9 secondary lateral branches. Length: About 4 to 30 cm. Diameter: About 2.5 mm to 1 cm. Internode length: About 1 to 1.5 cm. Aspect: Upright and outwardly spreading. Texture: Smooth, glabrous. Color: 144C.

*Foliage description.*—Arrangement: Alternate, simple; sessile. Length: About 3 to 4 cm. Width: About 1 to 2 cm. Shape: Pinnatifid, deeply and finely incised; three to six-lobed. Apex: Acute; four to six-parted. Base: Attenuate. Margin: Entire; deeply and finely incised. Texture, upper and lower surfaces: Smooth, glabrous. Venation pattern: Pinnate. Color: Developing foliage, upper surface: 137B. Developing foliage, lower surface: 137D. Fully expanded foliage, upper surface: 137B. Fully expanded foliage, lower surface: 137D. Venation, upper and lower surfaces: 137B.

Inflorescene description:

*Appearance.*—Single daisy composite inflorescence form with ligulate ray florets. Disc and ray florets develop acropetally on a capitulum. Inflorescences held upright on terminal and axillary peduncles. Inflorescences upright and perpendicular to the peduncles. Inflorescences persistent. Inflorescences faintly fragrant; pleasant.

*Flowering response.*—Under natural conditions, plant flower from spring to fall in Michigan; plants flower continuous during this period.

*Inflorescence longevity.*—Inflorescences last about one week on the plant.

*Quantity of inflorescences.*—Freely flowering; about 25 to 30 inflorescence buds and opened inflorescences per lateral branch.

*Inflorescence size.*—Diameter: About 4 to 5 cm. Depth (height): About 2 cm. Diameter of disc: About 1.25 cm. Receptacle diameter: About 1 cm. Receptacle height: About 2.5 mm.

*Inflorescence buds.*—Height: About 5 mm. Diameter: About 7.5 mm. Shape: Ovoid. Color: 163B.

*Ray florets.*—Quantity per inflorescence: About 17 to 20 arranged in a single whorl. Shape: Ligulate. Length: About 1.75 to 2 cm. Width: About 6 to 8 mm. Apex: Rounded. Base: Attenuate. Margin: Entire. Texture, upper and lower surfaces: Smooth, satiny. Aspect: Initially upright; when mature, about 90° from vertical; slightly reflexing with subsequent development. Color: When opening, upper and lower surfaces: 1C. Fully opened, upper and lower surfaces: 155D; towards base, 1D.

*Disc florets.*—Arrangement: Massed at the center of the inflorescence. Quantity per inflorescence: More than 100. Shape: Tubular, five-parted at apex; apex, acute; base, fused. Length: About 1 to 1.2 cm. Diameter: About 7 to 8 mm. Color, immature and mature: 13A.

*Involucral bracts* (*phyllaries*).—Quantity per inflorescence: About 20 to 24. Length: About 3 to 4 mm. Width: About 2 mm. Shape: Elliptic. Apex: Broadly acute. Base: Truncate. Margin: Entire. Texture, upper and lower surfaces: Glabrous, smooth. Color, upper and lower surfaces: 145A.

*Peduncle.*—Strength: Moderately strong; flexible. Aspect: Upright to about 45° from vertical. Length: Terminal peduncle: About 4 to 6 cm. Fourth peduncle: About 3.5 to 4 cm. Diameter: About 2 mm. Texture: Smooth, glabrous. Color: 144A.

*Reproductive organs.*—Androecium: Present on disc florets only. Quantity per floret: About five. Anther length: Less than 1 mm. Anther color: 13A. Amount of pollen: None observed. Gynoecium: Quantity per floret: One. Pistil length: About 2 mm. Stigma shape: Two-parted. Style length: About 1 mm.

*Seed/fruit.*—Seed and fruit production has not been observed.

Disease/pest resistance: Resistance to pathogens and pests common to Argyranthemums has not been observed on plants grown under commercial production conditions.

Temperature/weather tolerance: Plants of the new Argyranthemum have been observed to be tolerant to rain, wind, high humidity and to temperatures from −1 to 37° C.

It is claimed:

1. A new and distinct cultivar of Argyranthemum plant named 'Vanilla', as illustrated and described.

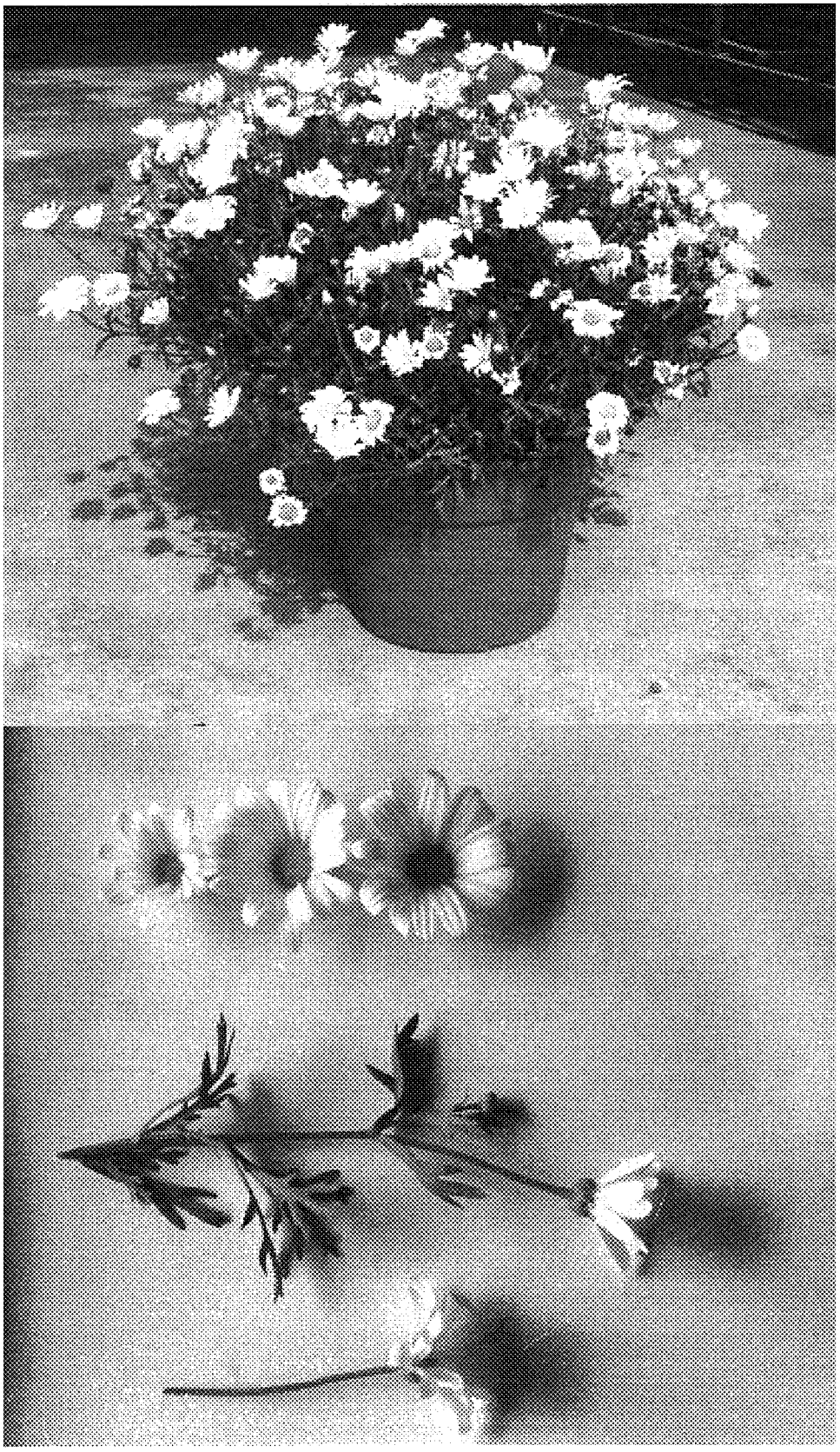

* * * * *